United States Patent
Grim et al.

(10) Patent No.: US 7,303,538 B2
(45) Date of Patent: Dec. 4, 2007

(54) VERSATILE ORTHOPAEDIC LEG MOUNTED WALKERS

(75) Inventors: Tracy E. Grim, Thousand Oaks, CA (US); Michael Stephen Skahan, Fillmore, CA (US); Hugo Antonio Cobar, Tarzana, CA (US); Joseph M. Iglesias, Thousand Oaks, CA (US)

(73) Assignee: Ossur hf, Reykjavik (IS)

( * ) Notice: Subject to any disclaimer, the term of this patent is extended or adjusted under 35 U.S.C. 154(b) by 374 days.

(21) Appl. No.: 10/201,124

(22) Filed: Jul. 23, 2002

(65) Prior Publication Data

US 2004/0019307 A1 Jan. 29, 2004

(51) Int. Cl.
*A61F 5/00* (2006.01)

(52) U.S. Cl. .......................... 602/23; 602/27

(58) Field of Classification Search ............... 602/23, 602/27, 60, 62, 16; 128/882
See application file for complete search history.

(56) References Cited

U.S. PATENT DOCUMENTS

| | | | |
|---|---|---|---|
| 1,639,381 A | 8/1927 | Manelas | |
| 3,878,626 A | 4/1975 | Isman | |
| 4,267,650 A | 5/1981 | Bauer | |
| 4,771,768 A | 9/1988 | Crispin | |
| 4,974,583 A * | 12/1990 | Freitas | 602/24 |
| 5,078,128 A | 1/1992 | Grim et al. | |
| 5,250,021 A | 10/1993 | Chang | |
| 5,329,705 A | 7/1994 | Grim et al. | |
| 5,355,562 A * | 10/1994 | Matoba et al. | 24/625 |
| 5,368,551 A * | 11/1994 | Zuckerman | 602/23 |
| 5,452,527 A | 9/1995 | Gaylord | |
| 5,464,385 A | 11/1995 | Grim | |
| 5,546,642 A * | 8/1996 | Anscher | 24/625 |
| 5,983,528 A | 11/1999 | Hartung | |
| 6,102,881 A | 8/2000 | Quackenbush et al. | |
| 6,155,998 A | 12/2000 | Gilmour | |
| 6,299,588 B1 * | 10/2001 | Fratrick | 602/27 |
| 6,345,454 B1 | 2/2002 | Cotton | |

FOREIGN PATENT DOCUMENTS

DE    26 51 089    5/1978

* cited by examiner

Primary Examiner—Michael A. Brown
(74) Attorney, Agent, or Firm—Bacon & Thomas, PLLC

(57) ABSTRACT

A versatile orthopedic walker includes a high strength engineered plastic base with spaced upper and lower surfaces and upwardly extending slotted strut supports. The base may be laterally and vertically cored, and an outer sole is provided which extends upward over the core openings, with the upper edges of the outsole being ridged to fit into a peripheral groove in the base to provide a smooth exterior surface. Struts of different lengths are provided, and all of the struts have identical arrangements for interlocking with the base. All of the struts may be provided with a three pronged construction to triply lock the struts into the base. The struts may have areas of reduced cross-section providing pivot points or areas of flexibility to accommodate different size patients, and limiting stops may be provided to assure adequate orthopedic support. Fully integrally molded pivoting D-rings may hold walker straps in place.

28 Claims, 12 Drawing Sheets

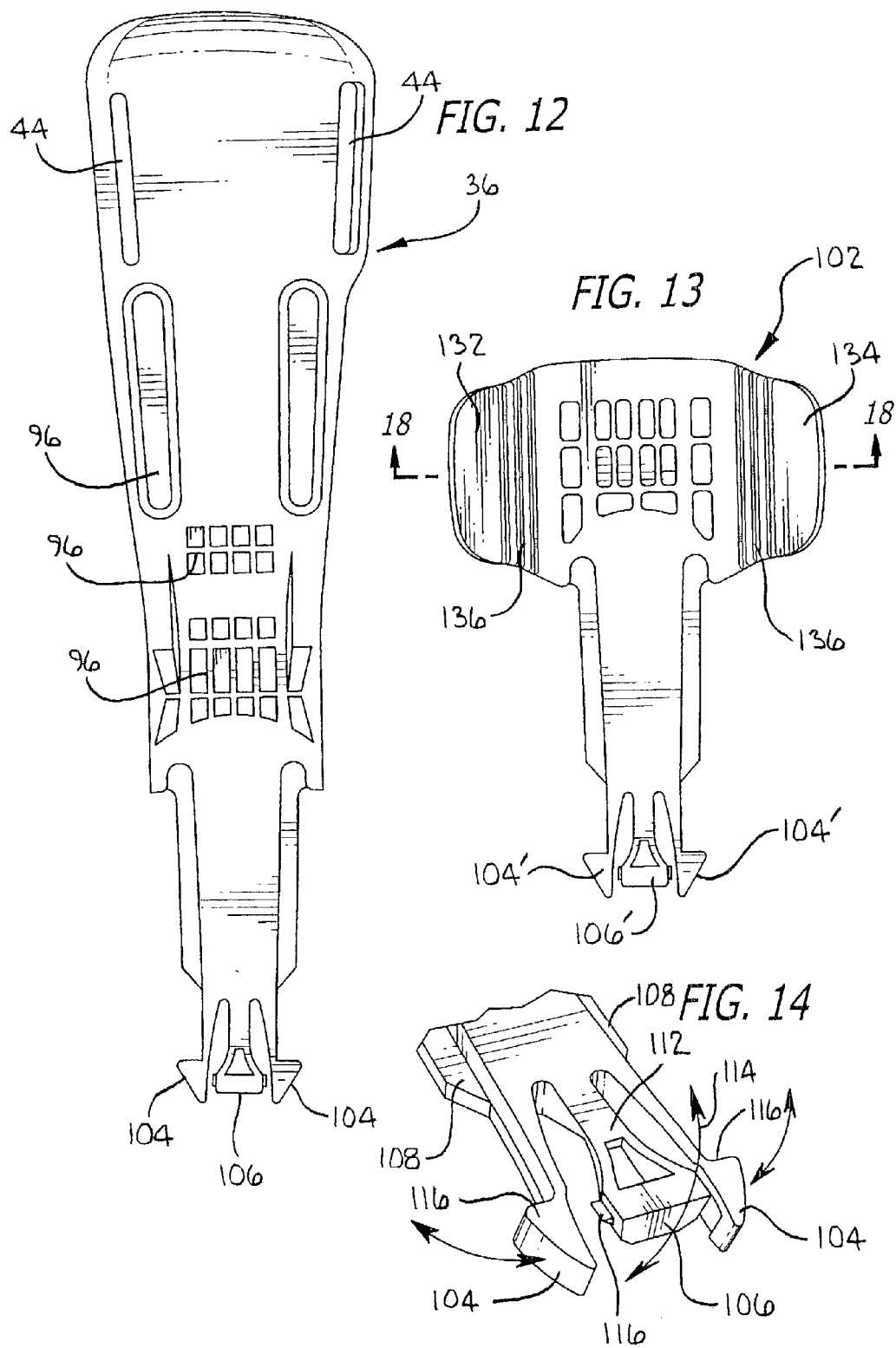

VERSATILE ORTHOPAEDIC LEG MOUNTED WALKERS

FIELD OF THE INVENTION

This invention relates to orthopedic walkers, which are orthopedic support boots which encompass the foot, ankle and lower legs, for use by persons recovering from injuries such as broken bones or other trauma of the lower leg, ankle or foot. This type of orthopaedic product is often referred to as a "short leg walker".

BACKGROUND OF THE INVENTION

Leg mounted orthopaedic walkers are well known, and typical patents disclosing such walkers include the following

| | |
|---|---|
| U.S. Pat. No. 5,368,5581 | Granted: Nov. 29, 1994 |
| Inventor: Zuckerman | |
| Title: Ankle Brace Walker | |
| U.S. Pat. No. 4,771,768 | Granted: Sep. 20, 1988 |
| Inventor: Crispin | |
| Title: Controlled Motion Ankle Fracture Walker | |
| U.S. Pat. No. 5,078,128 | Granted: Jan. 7, 1992 |
| Inventor: Grim et al. | |
| Title: Removable Leg Walker | |
| U.S. Pat. No. 5,329,705 | Granted: Jul. 19, 1994 |
| Inventor: Grim et al. | |
| Title: Footgear with Pressure Relief Zones | |
| U.S. Pat. No. 5,464,385 | Granted: Nov. 7, 1995 |
| Inventor: Grim | |
| Title: Walker with Open Heel | |

SUMMARY OF THE INVENTION

However, the known prior art walkers suffer from various shortcomings or disadvantages.

In this regard, the exteriors of some walkers are irregular so that they may catch on adjacent objects or fabric, and do not have an aesthetically pleasing configuration.

Concerning the struts which normally extend upwardly from the base of the walker, (1) they may not include readily interchangeable long and short struts; (2); they may not readily accommodate different size lower legs; (3) the mechanisms for securing the struts to the base may be either permanent, or subject to failure; (4) the flexibility of the struts may be substantially linear, and therefore may be too flexible throughout bending cycles to provide adequate orthopaedic support, or may be unduly stiff so as to irritate the user.

Regarding the walker bases, some available walkers do not have adequate resiliency to prevent undue shock during walking motion such as heel strike or other shock.

The walker base may have a substantially flat outer sole, or outsole, adhered to the lower surface of the base; and these substantially flat outsoles may be subject to delamination from the base.

In respect to the strap retaining loops or D-rings, the multipart units which are frequently employed for pivot applications are often unduly complex and expensive.

In accordance with one specific illustrative embodiment of the invention, a versatile walker which overcomes the shortcomings outlined hereinabove includes the following integral features:

1. The struts are secured to the base on a snap-in basis using a three pronged extension on the laser end of the struts, with the two outer prongs constituting locking members which fit into grooves and recesses in the base, with the third, central prong being resiliently biased toward the outer prongs so that when the two outer prongs lock into place, the central prong blocks their release.

2. Both long struts and short struts are provided, with identical locking arrangements on their lower ends, which may be of the type as outlined hereinabove.

3. The struts may be provided with reduced thickness zones to increase flexibility and to accommodate different anatomical configurations without sacrificing stability. Reduced thickness zones located below the upper end of the struts but at least an inch or two above the ankle joint can provide medial/lateral flexibility or hinge points to accommodate patients with relatively large lower legs. It is also noted that the medial/lateral hinge action may be provided by physical hinges or pivot points along the length of the strut, rather than by reduced strut thickness.

4. The struts may be provided either at the juncture with the base or along their length, with variable resiliency mechanisms, to permit initial easy deflection to accommodate minor deflections of the struts, and with arrangements for increasing resistance to deflections greater than a predetermined distance or angle. These arrangements may include reduced thickness in the struts, and a stop which is engaged when the deflection exceeds a predetermined amount.

5. The struts may have outwardly extending flaps or wings which may be hingedly secured to the central part of the strut, to accommodate various sizes of the patients' anatomies. So called "living hinges", or lines of reduced thickness, or grooves, extending partially through the plastic strut, may be employed to provide the hinging function.

6. The outer sole or outsole of the walker may include protrusions which may be hollow or doughnut shaped, in its upper surface to provide resiliency and cushioning during walking. And the outsole may extend upward around the outer periphery of the base, and have a peripheral bead interfitting with a mating recess in the base and providing a continuous smooth exterior surface at the junction between the outsole and the base. The base may be cored from the sides at the central area of the walker, and may be cored with relative small recesses from the top, toward the front and rear of the base, to reduce the weight of the walker. The outsole extends over the side core openings, thereby preventing the entry of foreign material, and provides a pleasing aesthetic appearance.

7. The strap retention loops or D-rings which are employed for pivoting functions are formed of one piece moldings, with the integral pivot pin pivotally locking the D-ring onto the plastic walker base.

It is to be understood that all of the foregoing features contribute to the realization of versatile walkers in which either long or short struts may be employed and which accommodate patients with different types of injuries, and patients with different anatomical configurations.

It is further noted that in some cases, instead of having separate struts secured to a base, the struts may be integrally molded with the base.

Advantages of the new design include the elimination of decorative side caps, increased outsole adhesion to the plastic base, resistance to water, mud and dirt, increased surface contact and gripping action, increased resiliency between outsole and plastic base and improved aesthetic appearance resulting from the smooth outer surface mating of the outsole and the plastic base. The upward extent of the oustsole of the base, and the interfitting recess and groove also prevents delamination of the outsole from the base. Variations in the size of the ankles and lower leg are accommodated by living hinges and by increased flexibility within preset angular limits. Safety is assured by the triple locking mating arrangements between the struts and plastic base. Finally, costs are reduced by the use of integrally molded d-rings which may provide pivoting action, by the simplification of the walker structure, and by avoiding the need for different walker configurations for different anatomical configurations.

Other objects, features and advantage will become apparent from a consideration of the following detailed description, and from the accompanying drawings.

BRIEF DESCRIPTION OF THE DRAWINGS

FIG. 12 is a side view of a long strut shown separate from the complete walker;

FIG. 13 is a view from the inside of a short strut which may be employed when the injury is confined to the ankle or lower ends of the lower leg bones;

FIG. 14 is a perspective view of the three prong locking mechanism for the struts;

DETAILED DESCRIPTION OF THE PREFERRED EMBODIMENTS

Figure 1:
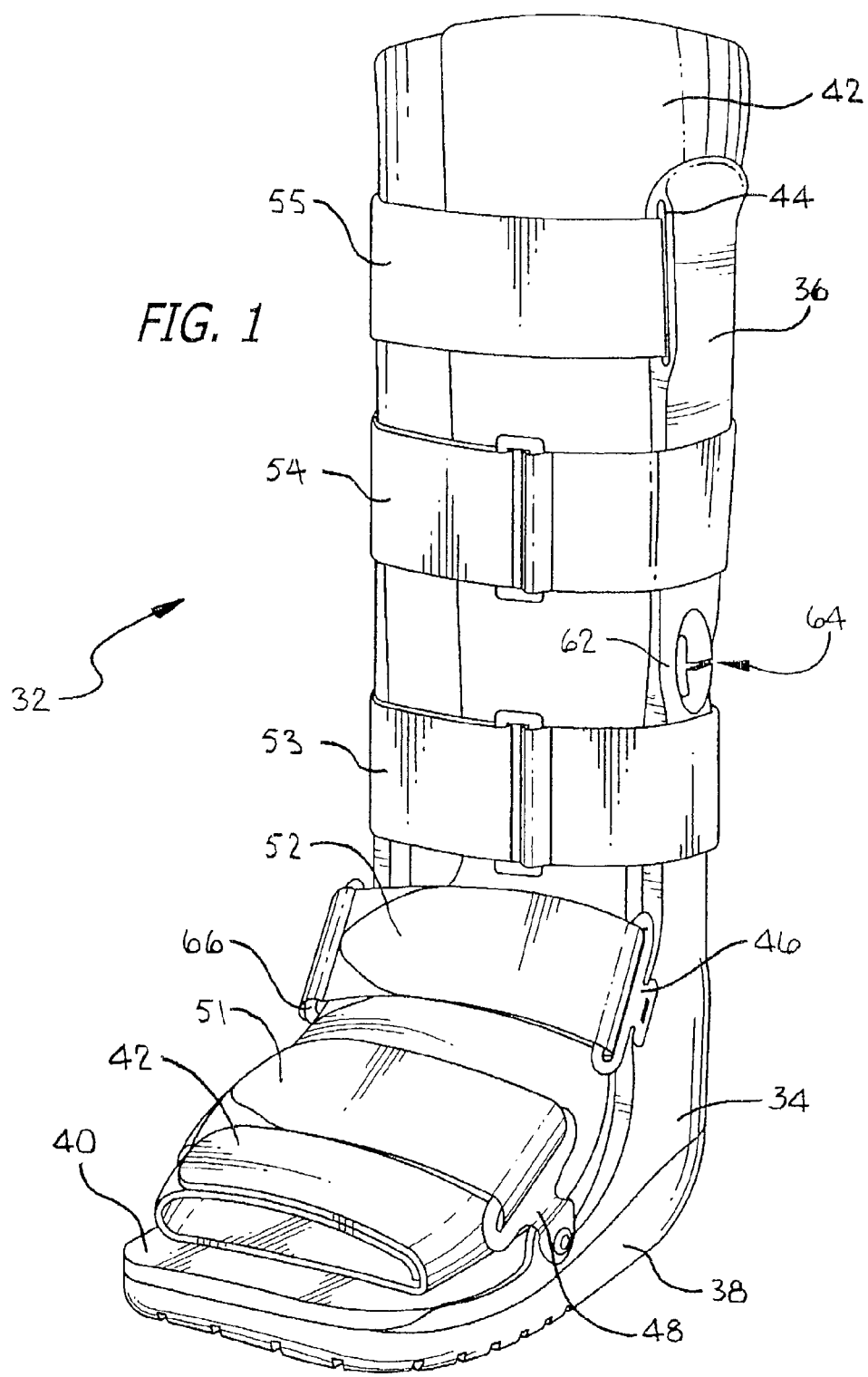
FIG. 1 is a perspective view of an orthopaedic walker illustrating the principles of the invention.
Figure 2:
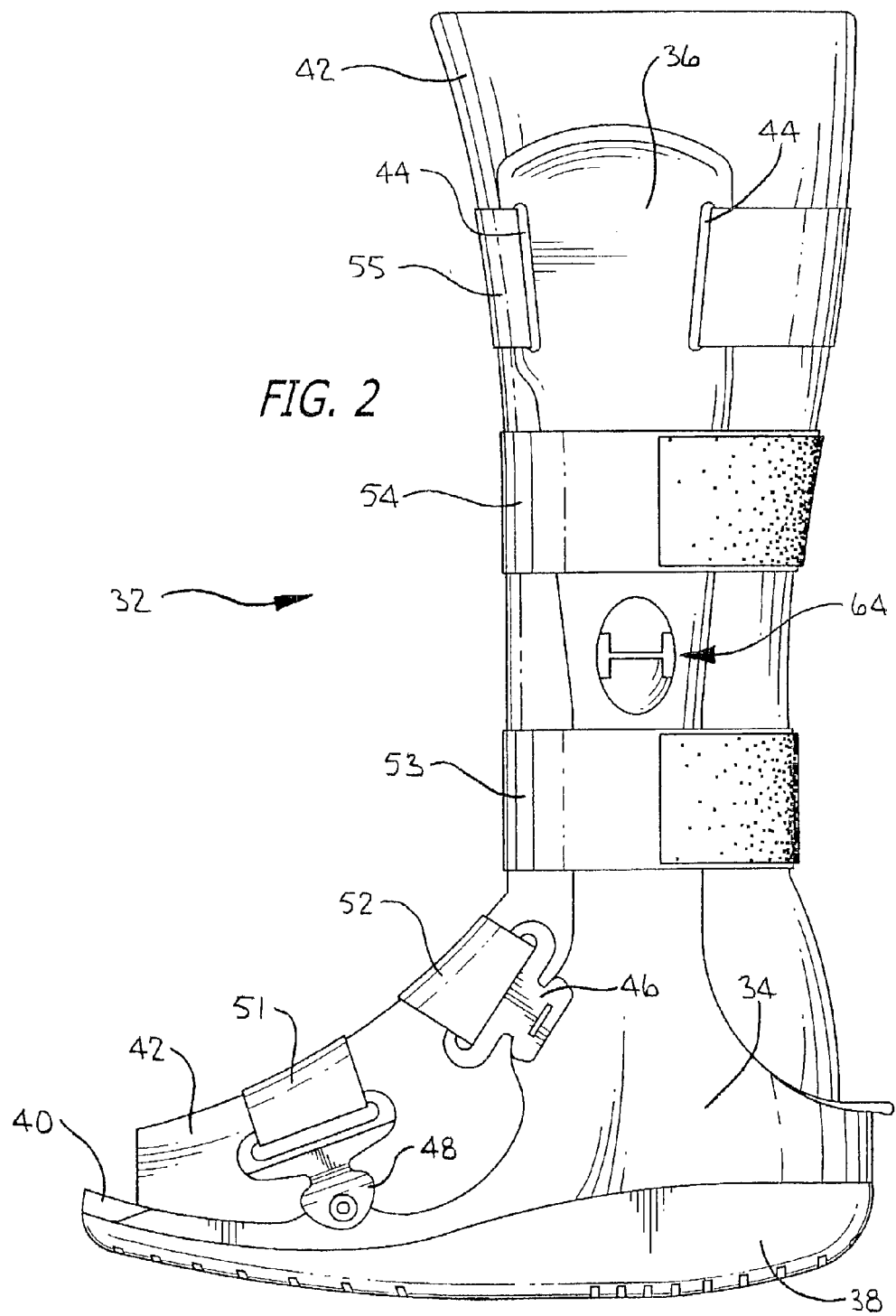
FIG. 2 is a left side elevational view of the walker of FIG. 1.

Referring more particularly to the drawings, FIG. 1 is a perspective view of a walker 32 illustrating the principles of the invention. The walker of FIG. 1 includes an engineered plastic base member 34, two struts, one of which is visible at reference 36, and an outersole, or outsole 38. The plastic base 34 may, for example be formed of fiber glass filled nylon, but other high strength plastics or other materials may be employed such as aluminum which may for example be powder coated. A resilient layer 40, which may be formed of one-quarter inch thick resilient foam, provides a cushion between the foot and the upper surface of the plastic base 34. Additional padding 42 extends around the foot, ankle and lower leg of the patient. The padding 42 is held in place between the struts including strut 36 by hook and loop material of the Velcro® type, with hook type material extending along the inner surface of the struts, and with the padding 42 either having mating loop material on its outer surface, or being of a type of fabric which will inherently mate with hook type material.

It may be noted in passing that FIGS. 1 through 6 of the drawings are substantially the same as the first six figures of a design patent application filed on Jul. 23, 2002, and entitled "Top and Sides of Resilient Orthopaedic Walker".

Continuing with the description of FIG. 1 of the drawings, the straps 51 through 55 extend around the padded foot, ankle and lower leg of the patient. They are secured to the base 34 and the struts by slots such as slot 44 in strut 36 or by D-rings, such as D-ring 46 or pivoted D-ring 48. The straps are provided with mating hook and loop material on their overlapping surfaces so that they are readily adjustable. The integrally formed D-ring 48 will be discussed in greater detail hereinbelow.

The strut 36 is reduced in thickness in the area 62 to increase the flexibility of the strut, to readily accommodate patients with large lower legs. However, to insure orthopaedic stability and support, a stop mechanism 64 is provided. As disclosed in greater detail hereinbelow (see FIG. 17), the stop mechanism 64 has two surfaces spaced apart by a narrow space. Accordingly, as the walker is being fitted to a person with a large lower leg, the upper portion of the strut 36 may easily flex outward. However, if in use, the strut 36 is flexed beyond a predetermined distance or angle, preferably at least equal to 15 degrees but less than 30 degrees, the two spaced surfaces at reference numeral 64 engage, and there is much higher resistance against further deflection, and increased support for the leg.

Concerning the straps 51 and 52, they each have one end permanently secured to a D-ring, with the D-ring 66 for strap 52 being visible. The free ends of straps 51 and 52 pass through D-rings 48 and 46, respectively and then fold back and engage facing surfaces of the straps by hook and loop securing material. The other straps 53, 54 and 55 similarly extend around the assemblies in a generally conventional manner with slots in the struts and/or hook and loop material on the outer surfaces of the struts holding the straps in place.

Figure 7:
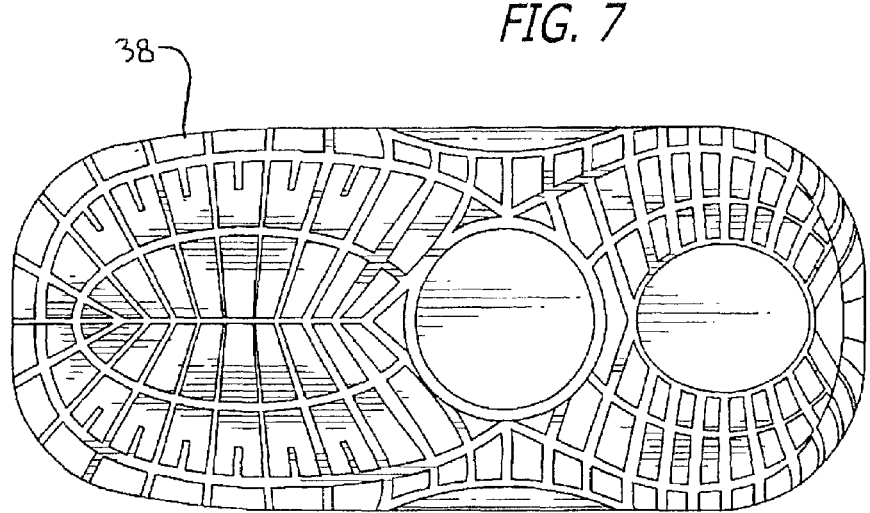

FIGS. 2 through 7 are various views of the walker as shown in FIG. 1, with FIG. 7 showing the patterned bottom layer of the outer sole, or outsole 38 for increased friction and traction. The outsole is bonded to the plastic base 34 by adhesive, and the outsole extends around and up the sides of the plastic base.

Figure 8:
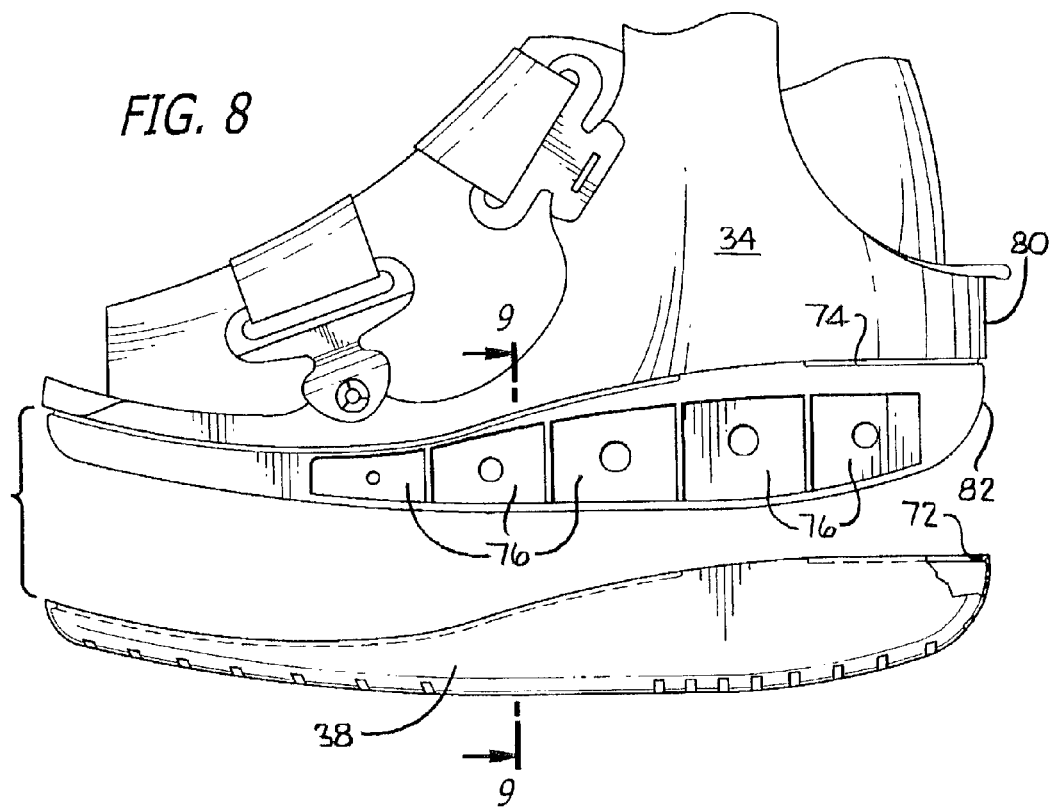
FIG. 8 is a partial exploded side view of the walker with the outer sole, or outsole spaced from the walker base.
Figure 9:
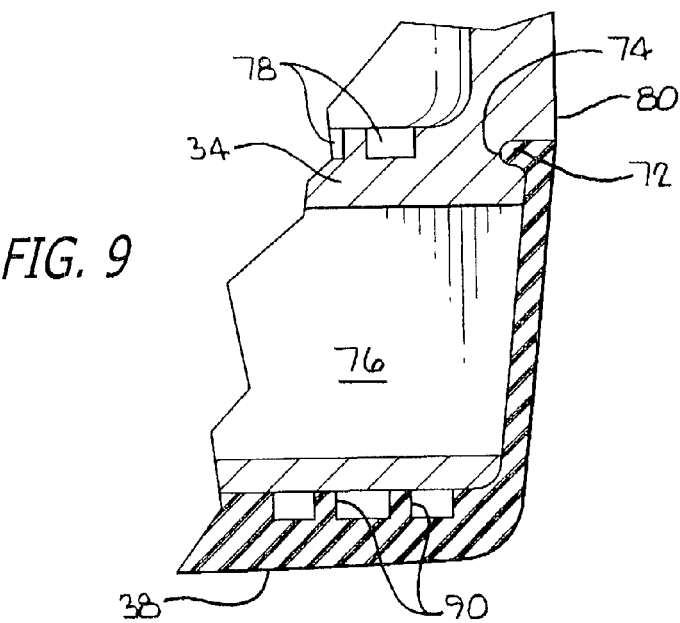
FIG. 9 is a partial cross sectional view showing the smooth interfit between the walker base and the outsole.

As shown to advantage in FIGS. 8 and 9 of the drawings, the upper edge of the outsole 38 has a ridge 72 which interlocks with a mating peripheral recess 74 in the base. This configuration increases traction and resists delamination of the outsole from the base. Instead of the simple ridge and groove as shown, more complex interlocking stuctures may be employed; and the ridge and groove may be reversed.

Referring to FIGS. 8 and 9 of the drawings, the cored openings 76 which extend inwardly to a thin central web, and the cores 78, are clearly shown. Referring back to FIGS. 1, 2 and 4 of the drawings, note that the outsole 38 covers the entry to the cored openings 76. This has the advantage of preventing ingress of mud or other foreign material.

It may also be noted that the outward extent of the walker base 34 in the area 80 just above the peripheral recess 74 is greater than the outward extent in area 82 just below recess 74, by a predetermined thickness equal to the thickness of the outsole 38. This configuration presents a smooth exterior in the area where the outsole 38 mates with the base 34; and has the advantages of avoiding protrusions which might catch on objects as the patient walks and also presents a pleasing aesthetic appearance. It also avoids the need for additional components for closing the ends of the cored areas 76.

Figure 10:
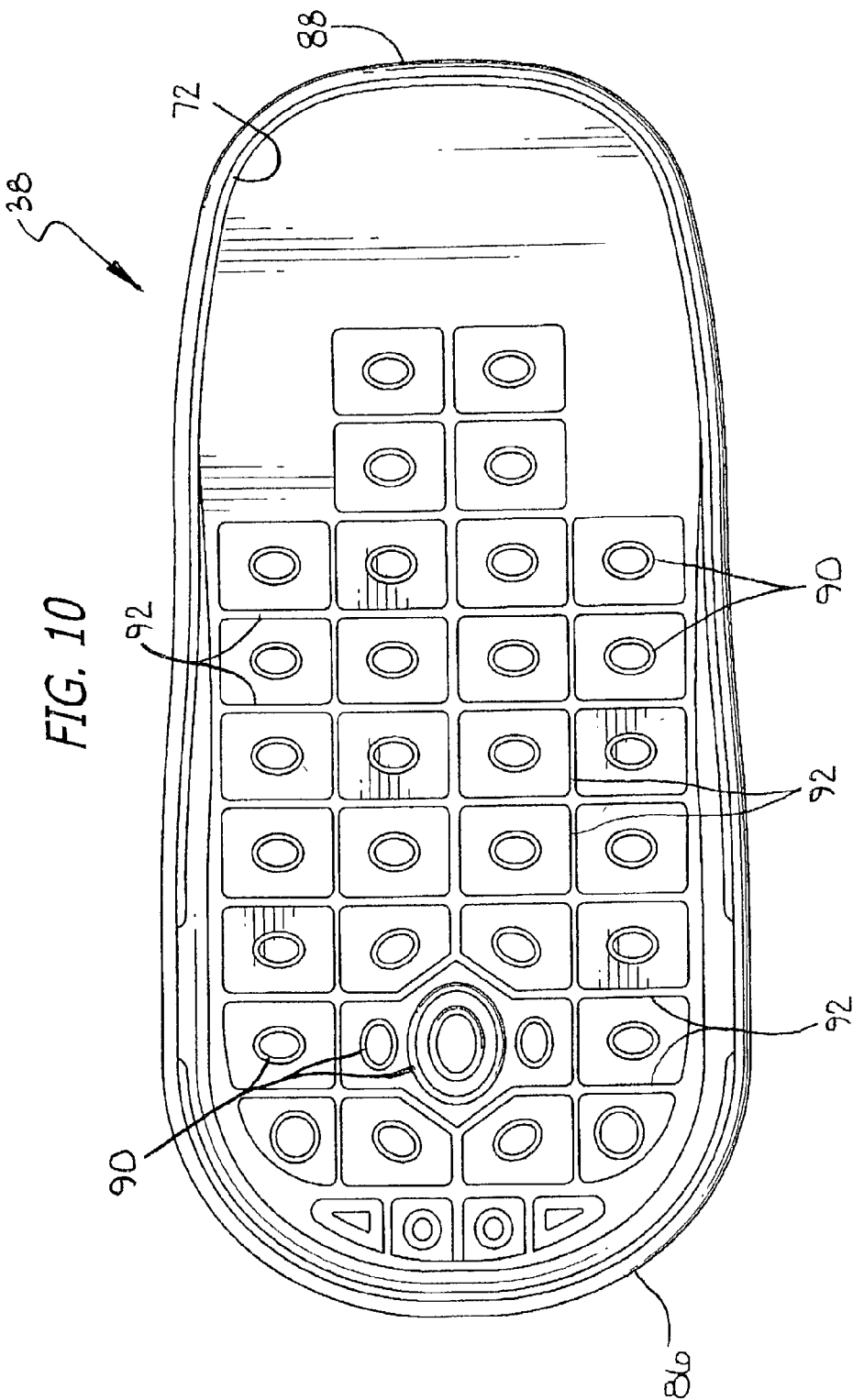
FIG. 10 is a top plan view of the outsole.

FIG. 10 is a top plain view of the outsole 38 with the heel area to the left as shown in FIG. 10 and the toe area to the right. This is a view of the inside of the outsole 38, and includes a large number of hollow doughnut shaped protrusions 90, and upwardly extending walls or ridges 92. These protrusions and walls extend upwardly from the continuous underlying surface of the outsole 38; and they provide additional resiliency particularly in the heel area, where the heel strike portion of a walking stride could otherwise provide a shock to the injured lower leg or foot of the patient. It is also noted that the closed wall protrusions trap air between the lower portion of the outsole and the mating surface of the base 34, thereby increasing the resiliency and buoyancy provided by the outsole. It is also noted that the outsole 38 is preferably adhesively bonded to the base 34.

Figure 11:
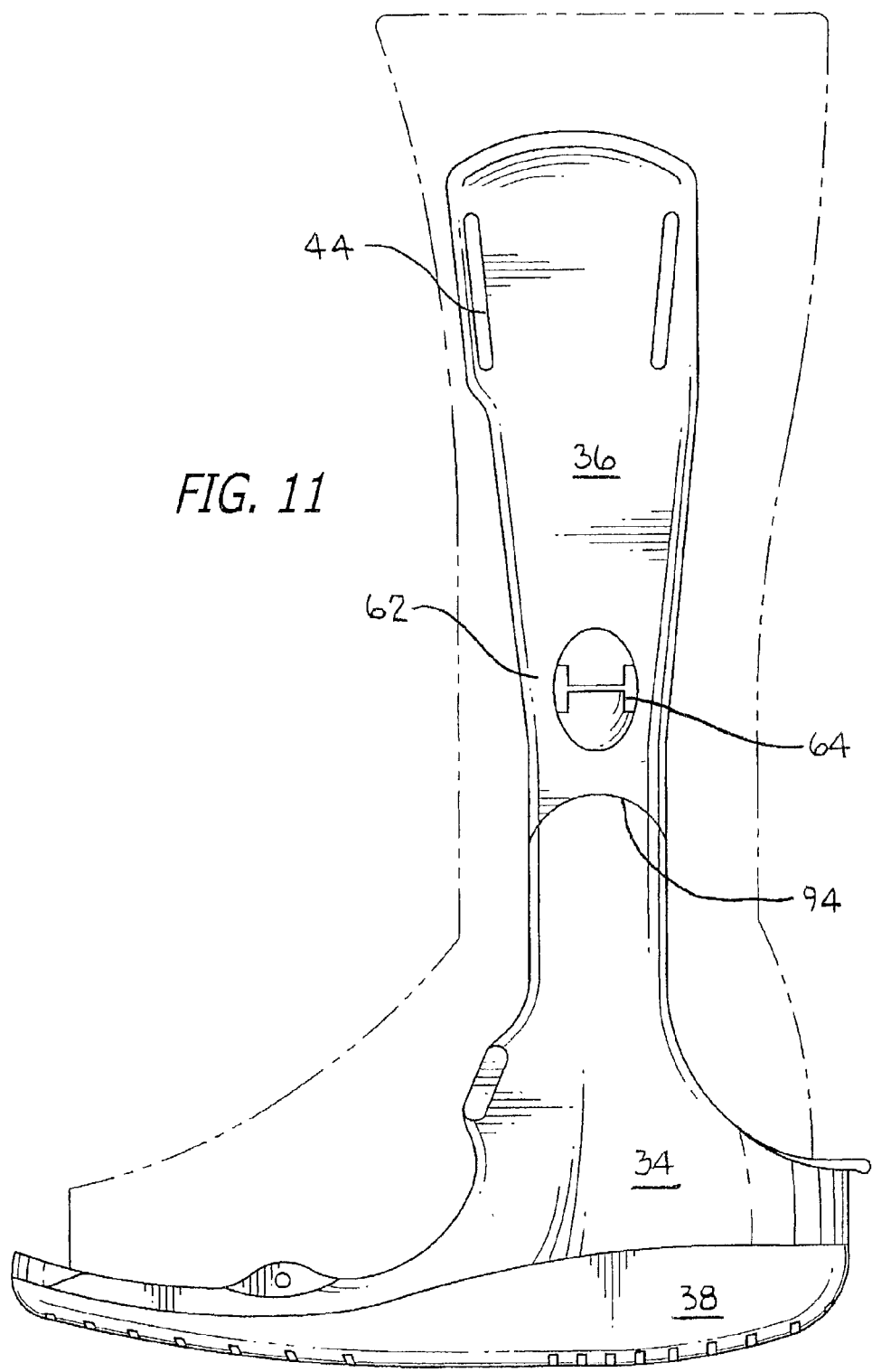
FIG. 11 is a side elevational view of the walker with the straps and padding removed.

FIG. 11 is a side view of the walker of FIG. 1 with the padding straps and D-rings removed. Apart from matters previously mentioned, the line 94 represents the mating surfaces between the strut 36 and the walker base 34.

FIG. 12 is a plan view of the inside of a long strut which is, by way of example and not of limitation, about 13 inches long. It includes openings or slots 44, and recesses 96 to reduce the weight of the assembly. As indicated in earlier figures of the drawings, the slots 44 receive straps, such as strap 55 for holding the walker securely onto the patient.

The short strut 102 shown in FIG. 13 of the drawings is about 6½ inches long, and, with its laterally extending wings 132 and 134, is about 4½ inches wide.

The lower end of the long strut 36 has a triple locking mechanism including three prongs, the two outer prongs 104, and a central locking prong 06. The short strut 102 has an identical three prong locking mechanism including the two outer prongs 104' and the central locking prong 106'.

Figure 15:
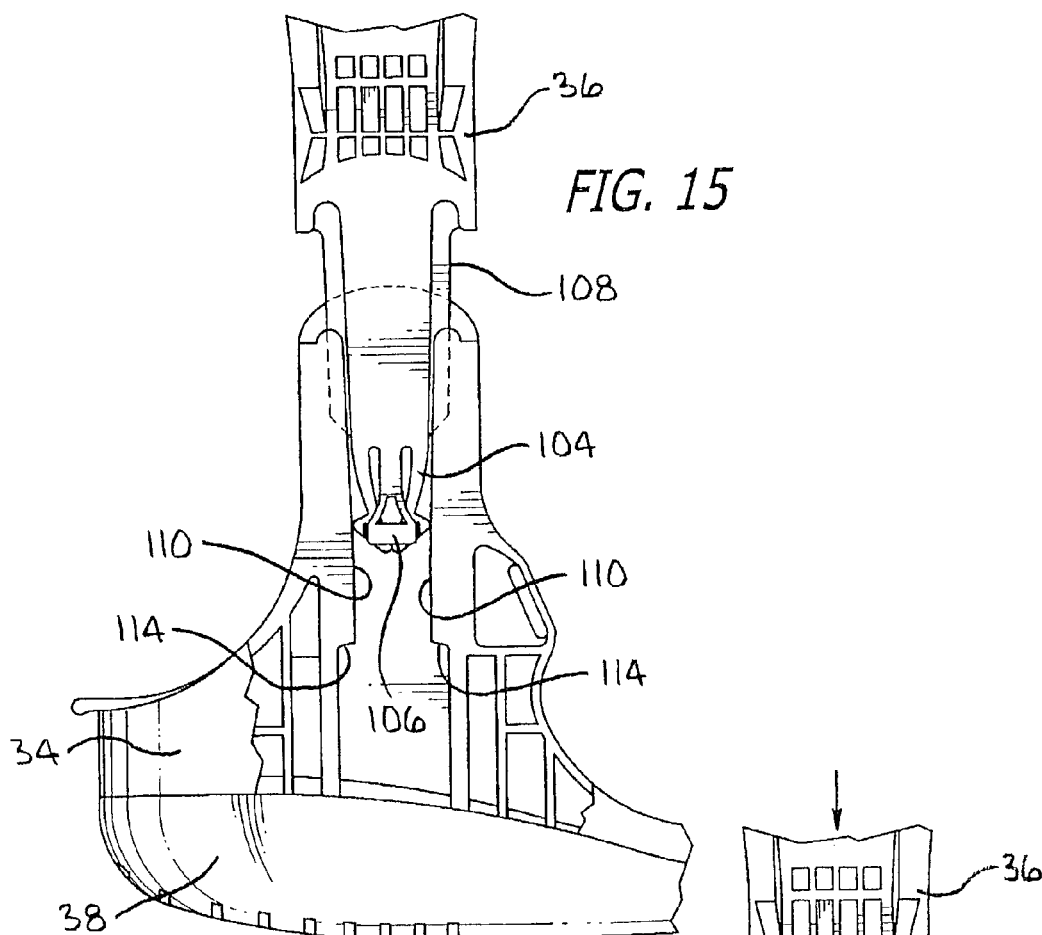
FIG. 15 is a fragmentary assembly drawing showing the strut partially assembled to the base.

FIG. 14 is a perspective view of the locking mechanism at the lower end of the struts. Note that, in addition to the three locking prongs, 104, 106, the struts have two thin outwardly extending longitudinal flanges 108 which mate with the longitudinal grooves or slots 110 on the strut support (see FIG. 15). Incidentally, it may be noted from FIG. 14 that the prongs 104,106 are thicker than the flanges 108, so that, as shown in FIG. 15, the ends of the prongs 104 do not slide in the grooves or slots 110, but ride on the outer edges of these slots 110. Incidentally the central portion 112 of the central locking prong 106 is of significantly reduced thickness, so that it may readily bend in the direction perpendicular to the plane of the strut, as indicated by arrow 114 in FIG. 14.

FIG. 15 shows the strut 36 partially assembled into the base 34, with the flanges 108 mating with slots or grooves 110. The outer prongs 104 are severely bent inward, and the central locking prong 106 is bent up out of the plane of the paper. The locking shoulders 114 are available to receive the outwardly extending surfaces 116 of the outer prongs 106 (see FIG. 14).

Figure 16:
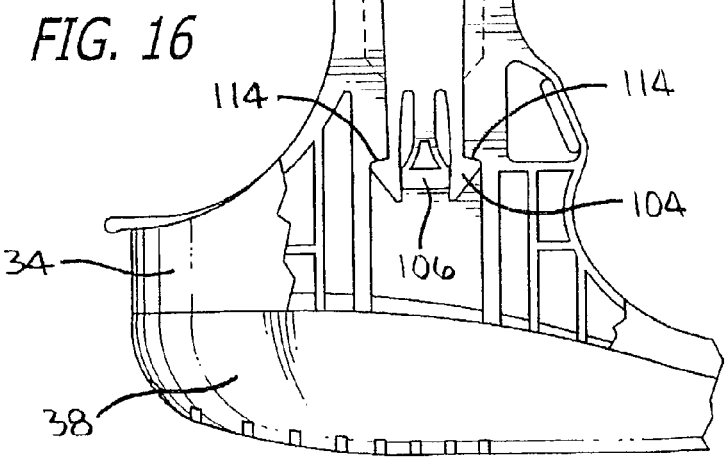
FIG. 16 is similar to FIG. 15 but shows the strut locking mechanism fully assembled and locked.

The fully locked position of the strut 36 is shown in FIG. 16, with the prongs 104 having surfaces 116 locked over the locking shoulders 114. The final locking step is accomplished by pressing the central locking prong 106 firmly into the space between the outer prongs 104 so that its outwardly extending protrusions 116 (see FIG. 14) interlock with recesses on the facing surfaces of the outer prongs 104.

As noted above, with both the long and the short walkers having identical locking mechanisms, a walker of either type may be formed using a common base, and the desired long or short struts.

Figure 3:
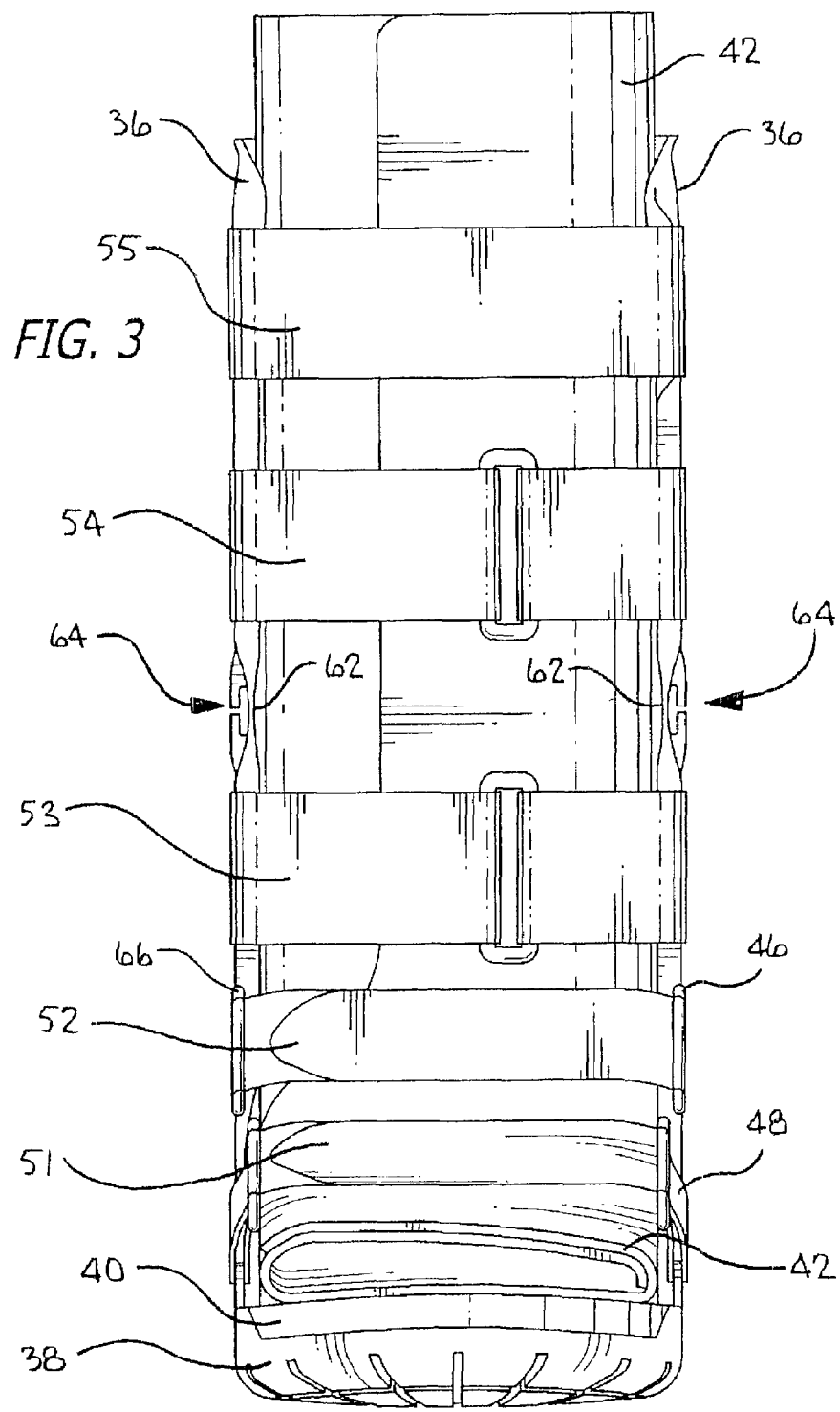
FIG. 3 is a front elevational view of the walker of FIG. 1.
Figure 4:
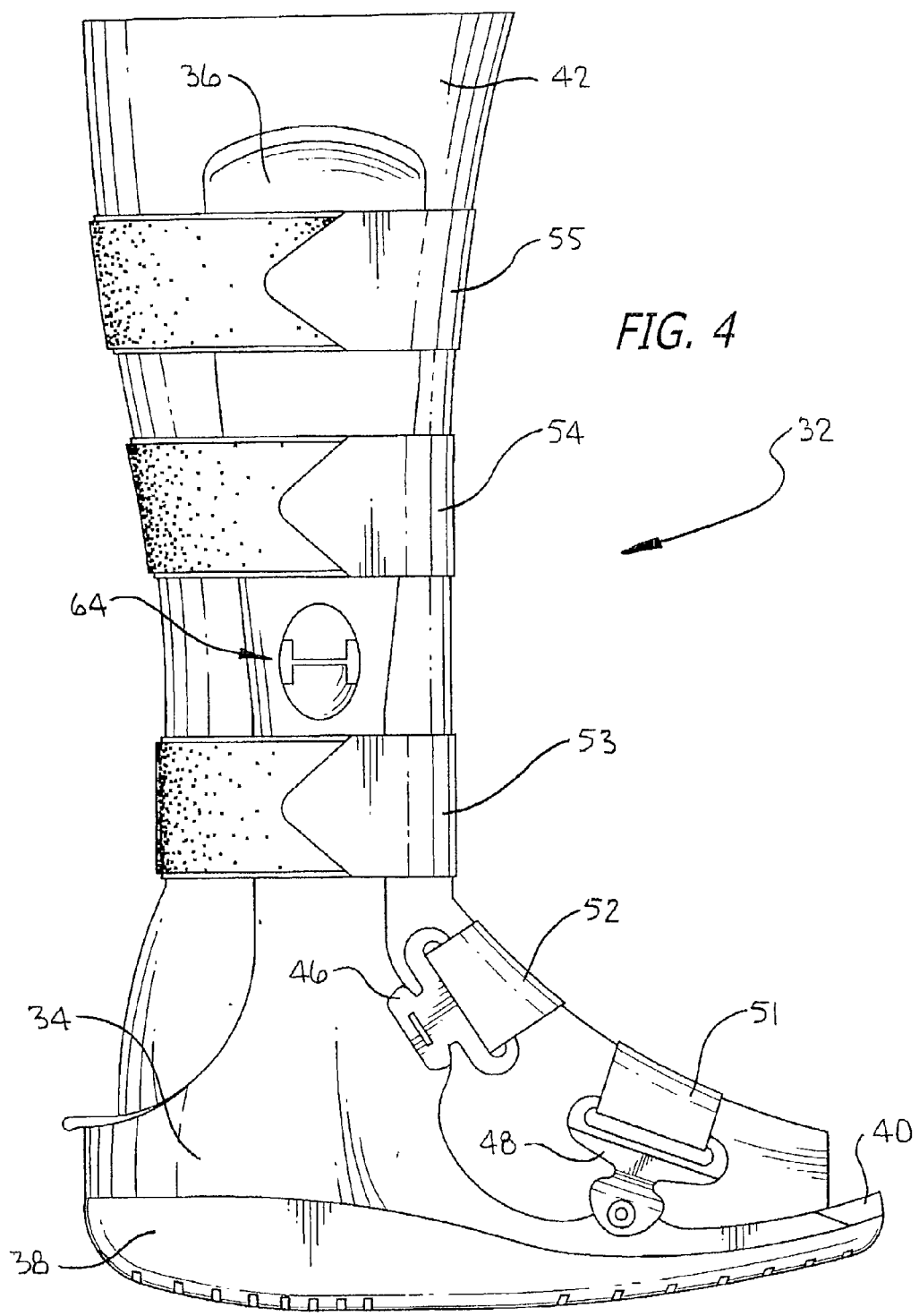
FIG. 4 is a right side elevational view of the walker of FIG. 1.
Figure 5:
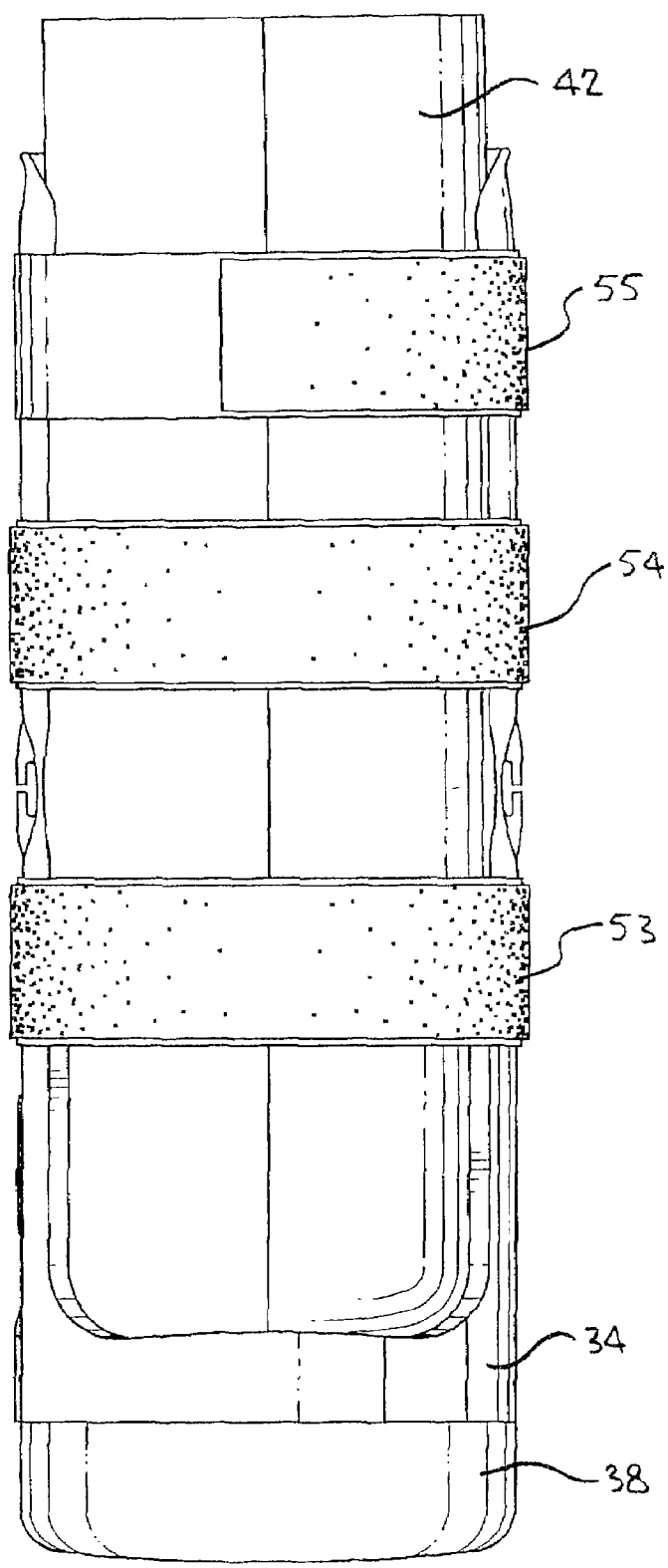
FIG. 5 is a rear elevational view of the walker of FIG. 1.
Figure 6:
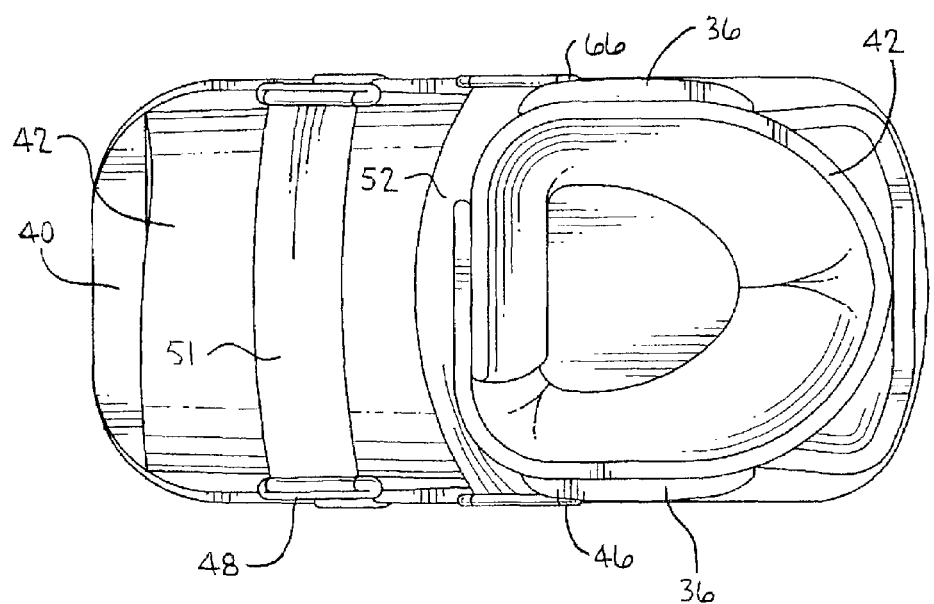
FIGS. 6 and 7 are top and bottom plan views of the walker.
Figure 17:
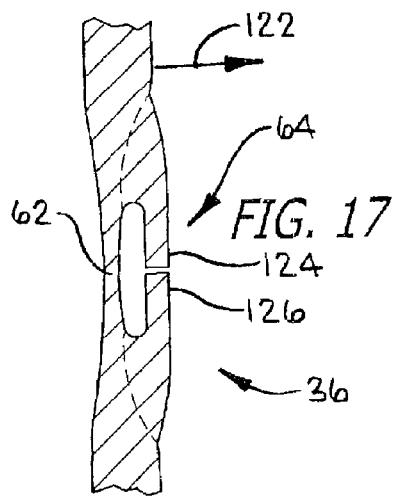
FIG. 17 is a partial cross-sectional view of one of the long struts showing the reduced cross-section, for increased flexibility and the limiting stop arrangements.

Attention is now directed to FIG. 17 which should be considered along with FIGS. 3 and 11 of the drawings. As mentioned above, the struts such as strut 36 may be thinned down in area 62, to increase flexibility to readily accommodate patients with varying size lower legs. However, following deflection in the direction indicated by arrow 122, the surfaces 124,126 engage, and provide the desired orthopaedic structural support. This combination of initial flexibility and subsequent increased stiffness and reduced flexibility both accommodate varying size lower legs, and also provides the desired orthopaedic support.

Figure 18:
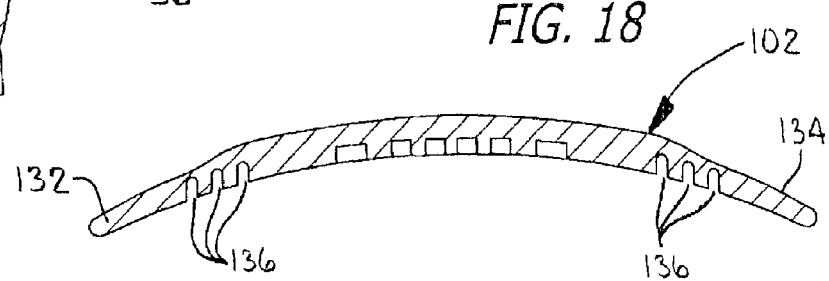
FIG. 18 is a transverse cross-section of one of the shorter struts showing the hinge lines of flexibility.

Referring now to the short walker strut of FIG. 13 and the cross-sectional view of FIG. 18, taken along plane 18-18 of FIG. 13, the short strut 102 is provided with laterally extending wings 132 and 134, with vertically extending lines of weakness or so-called "living hinges" 136. In practice two struts such as strut 102 are mounted on a walker base, with padding around the ankle of the type shown in FIGS. 1-6, but somewhat shorter, commensurate with the height of the struts. Straps are mounted to the struts and to the padding preferably using the hook and loop principle; and the wings 132, 134 on the short struts, are flexed to make a close supporting fit with the size of the foot and ankle of the patient.

Figure 19:
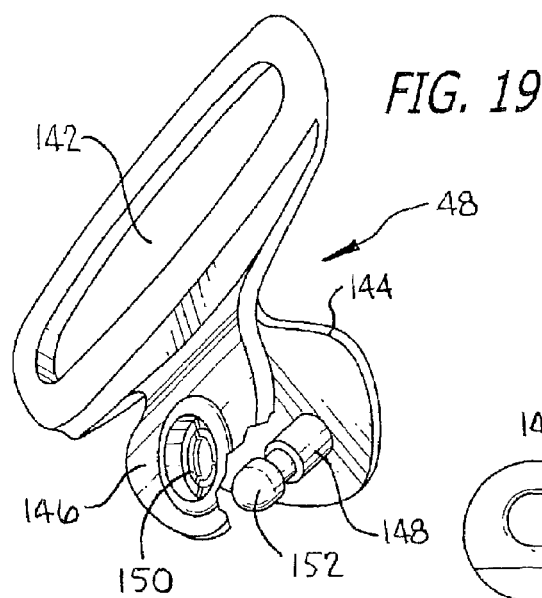
FIG. 19 is a perspective view of an integral pivotal "D-ring"
Figure 20:
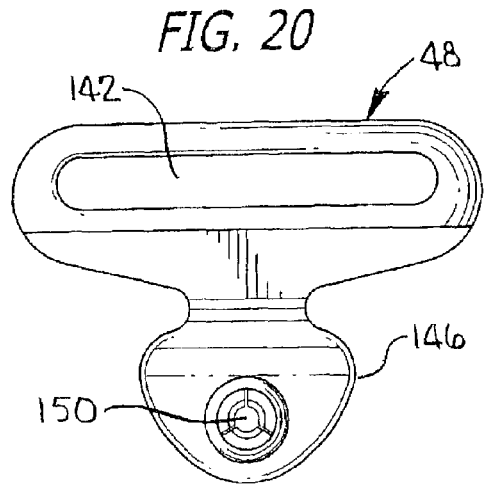
FIG. 20 is a partial elevational view of the D-ring of FIG. 19.

FIGS. 19 and 20 relate to the integrally moulded pivotal D-ring of the type shown at 48 in FIG. 1 of the drawings. In FIG. 19, the "D-ring" 48 has an opening 142 for receiving a strap, and two integrally molded flaps 144 and 146. The flap 144 has an integrally molded pivot pin 148 formed thereon; and the flap 146 has a variable size opening 150. As indicated in FIG. 20 the opening 150 has outwardly directed cuts so that the rounded head 152 of pin 148 can snap through the hole. The side walls of the hole will then snap back and engage the reduced diameter section of the pin and retain the pin in its closed position, normally locked into a hole in an orthopaedic walker or support as indicated in FIG. 1 of the drawings.

In closing, it is noted that specific illustrative embodiments of the invention have been shown in the drawings and described in detail hereinabove. It is to be understood that various changes and modifications may be made without departing from the spirit and scope of the invention. Thus, by way of example and not of limitation, the locations of the rib 72 and the recess 74 may be reversed with the rib on the base and the recess on the periphery of the outsole. Also, the outer prongs on the locking mechanism may be made thinner to fit into the grooves or slots on the strut supports of the base. In addition, the struts may be formed of aluminum over-molded with plastic, as one alternative to the use of fiber-glass impregnated nylon. In another area, the stop for reducing strut flexibility be included in the junction between the struts and the base, with one of the two mating stop surfaces being on the base, and the other stop surface being on the strut, and with the strut-to-base joint being somewhat flexible. Further, the outsole may be more permanently affixed to the walker base by over-molding the bottom of the base with the outsole, and having the outsole interlock into openings or recesses in the base. Also, the struts, either long or short, may be provided with slots, or integrally molded outwardly extending D-ring type structures for receiving straps. Accordingly the present invention is not limited to the specific embodiments shown in the drawings, or described in detail hereinabove.

We claim:

1. A versatile orthopaedic walker for mounting on the lower leg of a patient, comprising:
    a walker base of high strength materials:
    said base including two upwardly extending side strut supports having inner substantially vertically extending slots for receiving struts;
    said base having a central raised area for receiving the foot of a patient and a spaced lower substantially continuous surface for receiving an outer sole or outsole;
    said base being cored to reduce the weight thereof;
    said base having a peripheral inwardly directed groove extending substantially around the periphery thereof;
    the outer surface of said base having an outer surface above said groove extending outwardly by a predetermined distance as compared with the outer surface of said base below said groove;
    an outer sole, or outsole, extending over said lower surface of said base, the upper edge of said outsole having a mating ridge extending into said groove;
    said outer sole having a thickness at the periphery thereof substantially equal to said predetermined distance so that the outer surface of said base and outsole is substantially continuous without significant discontinuity at the upper edge of said outsole;
    first and second struts, and a triple locking mechanism for securing said struts into said slots in said strut supports;
    said struts including flexible structural arrangements involving reduced thickness of said struts for accommodating patients with varying anatomical configurations;
    said base and said struts being secured to the patient by straps;
    at least some of said straps being pivotally mounted to said base by fully integrally molded D-ring type mounts.

2. A versatile orthopaedic walker as defined in claim 1 wherein said struts include areas of reduced thickness for permitting low resistance initial flexing of said struts, and stops for substantially increasing resistance to flexing following angular deflection of a predetermined amount.

3. A versatile orthopaedic walker as defined in claim 1 wherein said struts have a central portion and have laterally extending side wings, and wherein said reduced thickness areas are living hinges which extend substantially vertically to permit flexing of said side wings relative to said central portion of said strut.

4. A plurality of versatile orthopaedic walkers as defined in claim 1 wherein the base and outsole of all of the walkers are substantially the same, and wherein some of the walkers include long struts which extend substantially up the calf of the patient, and others of the walkers include short struts which extend less than halfway up the lower leg of the patient; and wherein the strut-to-base locking mechanism of all of the walkers is substantially the same.

5. A versatile orthopaedic walker as defined in claim 1 wherein said triple locking mechanism includes two outer locking prongs and a central prong, wherein said two outer prongs are mechanically biased outwardly to engage said slots, and are displaced outwardly to lock said struts in place, and said central prong is biased to fit between said two outer locking prongs and maintain them in their locked position.

6. A versatile orthopaedic walker as defined in claim 5 wherein said outer locking prongs have outwardly extending locking hooks on the ends thereof.

7. A versatile orthopaedic walker as defined in claim 5 wherein said central prong and said two outer prongs have interlocking protrusions and recesses.

8. A versatile orthopaedic walker as defined in claim 1 wherein said base is cored from each side thereof, concurrently forming openings on the sides of said base; and wherein said outsole extends upward around said base covering said openings, thereby avoiding the entry of foreign material such as mud, and providing a clean aesthetically pleasing outer surface.

9. A versatile orthopaedic walker as defined in claim 1 wherein said base is cored downwardly from the raised area near the toe and heel areas of said base, and a resilient pad extends over said cores to provide a comfortable base for support of the patients foot.

10. An orthopaedic walker as defined in claim 1 wherein said D-ring type mounts include a ring having an opening therethrough for receiving a strap, first and second flaps extending from said ring, the first of said flaps carrying a pivot pin with an enlarged head, and the other of said flaps having an opening through it for receiving the head of said pivot pin, and said hole having a variable diameter whereby following the insertion of the head of said pin through said hole, the hole contracts and locks said pivot pin to extend between said two flaps.

11. A versatile orthopaedic walker for mounting on the lower leg of a patient, comprising:
    a walker base of high strength material: said walker including two struts extending upwardly from opposite sides of said walker base; first and second struts mounted to said strut supports;
    said base having a central area for receiving the foot of a patient and a spaced lower substantially continuous surface for receiving an outer sole;
    said base being cored to reduce the weight thereof; said base having a first peripheral linear interlocking construction extending substantially around the periphery thereof, the outer surface of said base having an outer surface above said linear interlocking construction extending outwardly by a predetermined distance as compared with the outer surface of said base below said construction;
    an outer sole, or outsole, extending over said lower surface of said base, the upper edge of said outsole having a second peripheral linear interlocking construction mating with said first interlocking construction;
    said outer sole having a thickness at the periphery thereof substantially equal to said predetermined distance so that the outer surface of said base and outsole is substantially continuous without significant discontinuities at the upper edge of said outsole.

12. A versatile orthopaedic walker as defined in claim 11 wherein said first linear interlocking construction is a groove and said second interlocking construction is a ridge.

13. A versatile orthopaedic walker as defined in claim 11 wherein said base is cored from each side thereof, concurrently forming openings on the sides of said base; and wherein said outsole extends upward around said base covering said openings, thereby avoiding the entry of foreign material such as mud, and providing a clean aesthetically pleasing outer surface.

14. A versatile orthopaedic walker as defined in claim 11 wherein said base is cored downwardly from the raised area near the toe and heel areas of said base, and a resilient pad extends over openings associated with said cores to provide a comfortable base for support of the patient's foot.

15. A versatile orthopaedic walker as defined in claim 11 wherein said outsole is resilient and wherein the upper surface of said outsole is provided with a plurality of protrusions to provide increased shock absorbing and resiliency between said outsole and said base.

16. A versatile orthopaedic walker as defined in claim 15 wherein said protrusions are hollow to trap air within said hollow protrusions and provide increased buoyancy as said outsole is compressed.

17. A versatile orthopaedic walker for mounting on the lower leg of a patient, comprising:
   a walker base of high strength material:
   said walker including two strut supports extending upwardly from opposite sides of said walker base;
   said base having a central raised area for receiving the foot of a patient and a spaced lower substantially continuous surface for receiving an outer sole or outsole;
   first and second struts mounted respectively on said strut supports; and
   said struts having a predetermined thickness in at least first and second areas, and said struts including flexible structural arrangements involving substantially reduced thickness of said struts between said first and second areas for accommodating patients with varying anatomical configurations;
   wherein the struts include areas of reduced thickness defined as recesses for permitting low resistance initial flexing of the struts, and a pair stops corresponding to each recess and defined as flanges overhanging a portion of the corresponding recess and engageable with one another for substantially increasing resistance to flexing following angular deflection of a predetermined amount.

18. A versatile orthopaedic walker as defined in claim 17 wherein said struts have a central portion and have laterally extending side wings, and wherein said reduced thickness areas are living hinges which extend substantially vertically to permit flexing of said side wings relative to said central portion of said strut.

19. A plurality of versatile orthopaedic walkers as defined in claim 17 wherein the base and outsole of all of the walkers are substantially the same, and wherein some of the walkers include long struts which extend substantially up the calf of the patient, and others of the walkers include short struts which extend less than half way up the lower leg of the patient; and wherein the strut-to-base mounting mechanism of each of the walkers is substantially the same.

20. A versatile orthopaedic walker for mounting on the lower leg of a patient, comprising:
   a walker base of high strength material:
   said base including two upwardly extending side strut supports substantially vertically extending slots for receiving struts;
   said base having a central raised area for receiving the foot of a patient and a spaced lower substantially continuous surface for receiving an outer sole or outsole;
   first and second struts and a triple locking mechanism for securing said struts into said slots in said strut supports; and
   said triple locking mechanism including two outer locking prongs and a central prong, wherein said two outer prongs are mechanically biased outwardly to engage said slots, and are displaced outwardly to lock said struts in place, and said central prong is biased to fit between said two outer locking prongs and maintain them in their locked position;
   wherein said outer locking prongs have outwardly extending locking hooks on the ends thereof.

21. In combination:
   an orthopaedic support or brace;
   straps for holding said orthopaedic support or brace onto a patient;
   D-ring type mounts for pivotally securing or mounting said straps to said support or brace; and
   said D-ring type mount including a ring having an opening therethrough for receiving a strap, first and second flaps extending from said ring, the first of said flaps carrying a pivot pin with an enlarged head, and the other of said flaps having an opening through it for receiving the head of said pivot pin, and said hole having a variable diameter whereby following the insertion of the head of said pin through said hole, the hole contracts and locks said pivot pin to extend between said two flaps.

22. A versatile orthopaedic walker for mounting on the lower leg of a patient, comprising:
   a walker base of high strength material:
   said walker including two struts extending upwardly from opposite sides of said walker base;
   said base having a central area for receiving the foot of a patient and a spaced lower substantially continuous surface for receiving an outer sole, or outsoles and upwardly extending side surfaces around the periphery thereof;
   a resilient outer sole, or outsole, extending over said lower surface of said base, and upward along the side surfaces of said base, firmly secured to said side surfaces; and
   the upper surface of said outsole is provided with a plurality of protrusions to provide increased shock absorbing and resiliency between said outsole and said base;
   wherein said protrusions are hollow to trap air within said hollow protrusions and provide increased buoyancy as said outsole is compressed.

23. In combination:
   a plurality of versatile orthopaedic walkers for mounting on the lower leg of a patient, each said walker comprising:
   (a) a walker base of high strength material;
   (b) said base including two upwardly extending side strut supports having inner substantially vertically extending slots for receiving struts;
   (c) said base having a central raised area for receiving the foot of a patient and a spaced lower substantially continuous surface for receiving an outer sole or outsole;
   (d) an outer sole extending over said lower surface of said base;
   (e) first and second struts, and a snap-in locking mechanism for securing each said strut into one of said slots in said strut supports; and the base and outsole of all of the plurality of walkers being substantially the same, and some of the walkers including long struts which extend substantially up the calf of the patient, and others of the walkers include short struts which extend less than halfway up the lower leg of the patient, and wherein the strut-to-base locking mechanism of all of the walkers is substantially the same.

24. A versatile orthopaedic walker for mounting on the lower leg of a patient, comprising:
a high strength engineered plastic walker base:
said base having a central raised area for receiving the foot of the patient and a spaced lower substantially continuous surface for receiving an outer sole or outsole;
said walker including two struts extending upwardly from opposite sides of said walker base;
said struts providing a basic level of flexibility permitting limited outward displacement of said struts;
and said walker further including a recess defined along each strut and stop surfaces corresponding to the recess, the stop surfaces defined as a pair of flanges overhanging the corresponding recess and engageable with one another following predetermined outward displacement of said struts to limit outward movement of said struts, to greatly increase the resistance to further displacement, and to provide orthopaedic support against excessive outward flexing of said struts.

25. A versatile orthopaedic walker for mounting on the lower leg of a patient, comprising:
a high strength engineered plastic walker base:
said base having a central raised area for receiving the foot of a spaced lower substantially continuous surface for receiving an outer sole or outsole;
said walker including two struts extending upwardly from opposite sides of said walker base; and
said struts having hinge points for providing medial/lateral hinging of said struts to accommodate patients with varying anatomical configurations;
said hinge points being located intermediate the ends of said struts, about two inches or more above the ankle joint or malleolus.

26. A versatile orthopaedic walker as defined in claim 25 wherein said pivot point is formed by a reduced thickness zone along said struts.

27. A versatile orthopaedic walker as defined in claim 25 wherein said struts with included hinge points provide medial/lateral hinging of said struts for an angular extent of at least 10 degrees from the vertical.

28. A versatile orthopaedic walker for mounting on the lower leg of a patient, comprising:
a walker base of high strength material:
said base including two upwardly extending side strut supports having inner substantially vertically extending slots for receiving struts;
said base having a central raised area for receiving the foot of a patient and a spaced lower substantially continuous surface for receiving an outer sole or outsole;
first and second struts and a triple locking mechanism for securing said struts into said slots in said strut supports; and
said triple locking mechanism including two outer locking prongs and a central prong, wherein said two outer prongs are mechanically biased outwardly to engage said slots, and are displaced outwardly to lock said struts in place, and said central prong is biased to fit between said two outer locking prongs and maintain them in their locked position;
wherein said central prong and said two outer prongs have interlocking protrusions and recesses.

* * * * *